United States Patent [19]

Silverman et al.

[11] Patent Number: 5,637,745

[45] Date of Patent: Jun. 10, 1997

[54] ORGANOMETALLIC COMPOUNDS AND POLYMERS MADE THEREFROM

[75] Inventors: Gary S. Silverman, Stockton, N.J.; Haewon L. Uhm, Collegeville, Pa.; Kenneth K. S. Tseng, Lawrenceville, N.J.

[73] Assignee: Elf Atochem North America, Inc., Philadelphia, Pa.

[21] Appl. No.: 380,095

[22] Filed: Jan. 30, 1995

[51] Int. Cl.$^6$ .................. C07F 1/08; C07F 3/00; C07F 15/00

[52] U.S. Cl. .................. 556/110; 556/7; 556/9; 556/13; 556/27; 556/28; 556/30; 556/118; 556/136; 556/138; 523/132

[58] Field of Search .................. 556/7, 9, 13, 27, 556/28, 30, 110, 118, 136, 138; 523/132

[56] References Cited

U.S. PATENT DOCUMENTS

| | | | |
|---|---|---|---|
| 3,859,092 | 1/1975 | Gysling et al. | 204/15 |
| 3,860,501 | 1/1975 | Gysling | 204/15 |
| 3,927,055 | 12/1975 | Gysling | 260/438.1 |
| 4,286,988 | 9/1981 | Castelli et al. | 106/15.05 |
| 4,532,269 | 7/1985 | Gitlitz et al. | 523/122 |

FOREIGN PATENT DOCUMENTS

| | | |
|---|---|---|
| 64-16809 | 10/1989 | Japan. |
| 2110707 | 6/1983 | United Kingdom. |

OTHER PUBLICATIONS

T. Tanaka, "Effect of Heavy Metal Ions on Polymerization of Methyl Methacrylate Initiated by the Hydroxylamine–$H_2O_2$," Nippon Kagakukaishi, (4), pp. 591–594, 1986.

M.H. Gitlitz, "Recent Developments in Marine Antifouling Coatings," A Journal of Coatings Technology Reprint.

Borowski et al., J. Chem. Soc. Dalton Trans., 1990, pp. 29–34.

Borowski et al., J. Chem. Soc. Dalton Trans., 1991, pp. 1929–1935.

*Primary Examiner*—Porfirio Nazario-Gonzalez
*Attorney, Agent, or Firm*—Finnegan, Henderson, Farabow, Garrett & Dunner

[57] ABSTRACT

Compounds of formula (I) are disclosed:

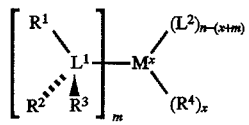

wherein $L^1$ is a main group atom, $L^2$ is a neutral ligand, M is a transition element or a metal element of Group 13, 14, 15, or 16 of the Periodic Table, x is the number of coordination sites of M, $R^1$ is a polymerizable group, $R^2$, $R^3$, and $R^4$ are ligands, and $R^5$ is an anionic ligand. The compounds or monomers of formula (I) are capable of conversion to polymers by combination with one or more other known monomers, such as methyl methacrylate. Such polymers can then be added as a binder in a paint formulation to make marine antifouling coating compositions. Also described is a method to prevent fouling on surfaces wherein a composition containing a metal complex compound of formula (II):

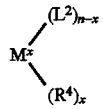

wherein M, x, $L^2$, n, and $R^4$ have the same meaning as in formula (I), is applied to the surface susceptible to fouling.

43 Claims, No Drawings

ORGANOMETALLIC COMPOUNDS AND POLYMERS MADE THEREFROM

BACKGROUND OF THE INVENTION

The present invention relates to novel compounds that are particularly useful in marine antifoulant coating compositions.

Marine fouling on ships and marine structures has been a problem for thousands of years. This problem has been recently addressed primarily by the use of certain coatings containing biocides that are toxic to marine organisms. These conventional coatings leached biocides out of the coating when in seawater.

Such a paint system, however, fails to provide a desired constant toxicant release, and moreover, does not advantageously erode in service. This is due to the selective extraction of the water-soluble component and consequent leaching of the toxicant from the interior of the paint film. A matrix of the insoluble resin component remains behind after the water-soluble component of the film (gum rosin) is leached away. Moreover, the spent paint film no longer controls fouling even though it might contain up to 30–40% of the initial level of toxicant because water penetration required for leaching the toxicant to the surface is limited through the matrix of residual resin. Spent antifouling systems of this type do not provide a suitable base for repainting since they possess poor mechanical properties due to the voids in the film resulting in poor adhesion of the new paint film.

Attempts to incorporate toxicants into water soluble polymers and to use these as antifouling paints have also failed to produce the desired results. Such paints swell in seawater and cannot be expected to provide good mechanical properties and uniform control of fouling since the whole paint film is weakened on prolonged water immersion.

In recent years, so-called self-polishing antifouling coatings have become increasingly popular. These coatings are based on polymers of tributyltin methacrylate, methyl methacrylate, and film softening monomers such as 2-ethylhexyl acrylate. The organotin polymer acts as the paint binder. All such paints also contain a toxicant additive such as cuprous oxide or a triorganotin compound. In addition, the usual paint additives such as pigments, thixotropic agents, etc. may also be present. In normally alkaline seawater, the polymeric organotin binder is gradually hydrolyzed and the tributyltin is liberated in a form that is an active antifoulant. The hydrolyzed polymer formed is water-soluble or water-swellable and is easily eroded off the surface by moving seawater, exposing a fresh surface of paint. The major advantage of these systems is that, unlike leaching paints, toxicant release is linear with time and all of the toxicant present is utilized over the lifetime of the paint. Furthermore, there is no need to remove the residues of an old self-polishing paint system prior to repainting, since the composition of the residue is essentially the same as it was when originally applied unlike conventional antifouling paints which leave a weak, leached-out matrix of binder on the ships' hull at the end of their lifetime. An additional advantage claimed for such systems is a reduction in hull surface roughness with time as a consequence of erosion of the paint film. This roughness reduction translates to fuel savings for the ship operator.

Sea-going vessels usually have between 2 and 4 coats of antifouling paint, each coat of 100 microns film thickness, applied to the hull. This coating, of 200 to 400 microns total film thickness, is expected to last for about five years.

A marine antifoulant coating should preferably meet some criteria in order to be commercially acceptable, such as:

1. The polymer is preferably soluble in a paint media for easy application;
2. The polymer solution preferably has good film-forming properties;
3. The film coating preferably has good adhesion to the ship's surface and is flexible;
4. The film preferably undergoes hydrolysis only at the coating surface. This permits the controlled release of the metal. The remaining paint surface becomes susceptible to the moving seawater and is eroded. This mechanism is known as "self-polishing" and a marked improvement in the ship's fuel efficiency is observed; and
5. The polymer preferably has controlled release characteristics.

Accordingly, the present invention is directed to novel compounds and marine antifoulant coating compositions containing polymers polymerized from these compounds.

Additional features and advantages of the present invention will be set forth in the description which follows, and in part will be apparent from the description, or may be learned by practice of the present invention. The objectives and other advantages of the present invention will be realized and attained by means of the elements and combinations particularly pointed out in the written description and appended claims.

SUMMARY OF THE INVENTION

To achieve these and other advantages and in accordance with the purpose of the present invention, as embodied and broadly described herein, the present invention relates to a compound of formula (I):

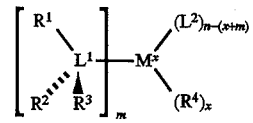

In this formula, $L^1$ is a main group atom. M is a transition element of the Periodic Table. Alternatively, M is a metal element of Group 13, 14, 15, or 16 of the Periodic Table. x is the oxidation state of M, n is the number of coordination sites on M, and m represents the number of $(R^1\ R^2\ R^3)\ L^1$ ligands bonded to M, which is usually 1.

$R^1$ is a polymerizable group.

$R^2$ and $R^3$, which can be the same or different, are a substituted or unsubstituted alkyl of up to 15 carbons; a substituted or unsubstituted aryl of up to 30 carbons; a substituted or unsubstituted alkoxy or thioalkyl of up to 15 carbons; a substituted or unsubstituted aryloxy or thioaryl of up to 20 carbons; an oxygen or sulfur containing heterocycle of up to 25 carbons; a substituted or unsubstituted amine; a substituted or unsubstituted amide; or a substituted or unsubstituted nitrogen heterocycle of up to 25 carbons when $L^1$ is not N.

$R^4$ is an anionic ligand and can be the same or different when x is greater than 1.

Lastly, $L^2$ is a neutral ligand group.

In another aspect, the present invention includes polymerizing one or more of the above compounds of formula (I) for use in marine antifoulant coatings as a binder which may also be effective as a co-biocide.

The present invention also relates to controlled release compositions containing polymers obtained by polymerizing monomers of formula (I).

In addition, the present invention relates to methods to prevent fouling on surfaces by applying a composition containing a compound of formula (II):

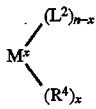

wherein M, x, $L^2$, n, and $R^4$ have the same meanings as in formula (I).

It is to be understood that both the foregoing general description and the following detailed description are exemplary and explanatory only and are not intended to provide further explanation of the present invention, as claimed.

DETAILED DESCRIPTION

One aspect of the present invention relates to the novel compounds of formula (I):

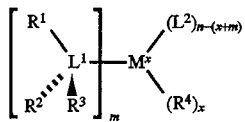

Compounds of formula (I) can also be considered monomers since these compounds are capable of conversion to polymers by combination with the same monomer or any other monomers capable of addition to the polymer. Polymers resulting from the polymerization of one or more compounds of formula (I) with any other known monomer, such as methyl methacrylate, can then be added as a binder in a paint formulation to make marine antifouling coating compositions.

Referring to formula (I), $L^1$ is a main group atom or element that preferably is a Group 15 element of the Periodic Table. $L^1$ can also be a Group 13, 14, or 16 element of the Periodic Table. All groups of the Periodic Table referred to herein are with reference to the "New Notation" of the Periodic Table set forth in Hawley's Condensed Chemical Dictionary 11th Ed. Thus, $L^1$ is preferably nitrogen, phosphorus, arsenic, antimony, or bismuth. Most preferably, $L^1$ is phosphorus.

m represents the number of $(R^1 R^2 R^3) L^1$ ligands bonded to M. m is usually 1 except for the following exceptions.

m is 2 when M is Cu, x is 1, $L^1$ is phosphorus, $L^2$ is not present (i.e., n−(x+m) is zero) and $R^4$ is cyanate, thiocyanate, and isocyanate; and m is 3 when M is Cu, x is 1, $L^1$ is phosphorus, $L^2$ is not present (i.e., n−(x+m) is zero), and $R^4$ is a substituted or unsubstituted thioalkyl having up to 15 carbons or a substituted or unsubstituted thioaryl having up to 25 carbons.

M is a transition element of the Periodic Table (i.e., Groups 3–12 of the Periodic Table).

Alternatively, M is a metal element of Groups 13–16 of the Periodic Table. In other words, M can be Sc, Y, La, Ac, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, Hg, Al, Ga, In, Tl, Ge, Sn, Pb, Sb, Bi, Si, As, Te, or Po.

Preferably, M is copper, zinc, or tin. Most preferably, M is copper.

x represents the oxidation state of M. n is the number of coordination sites on M. As presently known with regard to coordination sites in existing elements encompassed by M, n can be a whole number from 2 to 9 depending on M. For instance, where M is a Group 3 element, which includes Sc and Y,
 M has a coordination number of either 4 or 6 (mainly 6); and
 M has an oxidation state of +2, +3, +4 (mainly +3).
where M is a Group 4 element,
 M has a coordination number of 4, 5, 6, 7, or 8 (mainly 4 or 6); and
 M has an oxidation state of +4.
where M is a Group 5 element,
 M has a coordination number of 4, 5, 6, 7, 8, or 9 (mainly 6); and
 M has an oxidation state of +3, +4, or +5.
where M is a Group 6 element,
 M has a coordination number of 3, 4, 5, or 6 (mainly 6); and
 M has an oxidation state of +2, +3, +4, +5, or +6 (mainly +2 and +3).
where M is a Group 7 element, which includes Mn, Re, and Tc,
 M has a coordination number of 4, 5, 6, or 7 (mainly 4 and 6); and
 M has an oxidation state of +2, +4, +5, or +7.
where M is a Group 8 element,
 M has a coordination number of 3, 4, 5, 6, 7, or 8 (mainly 6); and
 M has mainly oxidation states of +2, +3, +4, and +6.
where M is a Group 9 element,
M has a coordination number of 4, 5, or 6; and
M has mainly oxidation states of +1, +2, +3, or +4.
where M is a Group 10 element,
 M has a coordination number of 4 or 6; and
 M has mainly oxidation states of +2 and +4.
where M is a Group 11 element,
 M has a coordination number of 2, 4, or 6; and
 M has mainly oxidation states of +1 and +2.
where M is a Group 12 element,
 M has a coordination number of 2, 4, or 6; and
 M has an oxidation state of +2.
where M is a Group 13 metal element, which includes Al, Ga, In, and Tl,
 M has a coordination number of 3, 4, 5, or 6; and
 M has an oxidation state of +2 or +3 (mainly +3).
where M is a Group 14 metal element, which includes Si, Ge, Sn, and Pb,
 M has a coordination number of 4, 5, or 6; and
 M has an oxidation state of +2 or +4.
where M is a Group 15 metal element which includes As, Sb, and Bi,
 M has a coordination number of 3, 4, 5, or 6; and
 M has an oxidation state of +3 or +5.
where M is a Group 16 metal element, which includes Te and Po,
 M has a coordination number of 4, 5, or 6; and
 M has an oxidation state of +2, +4, or +6.

$R^1$ is a polymerizable group. In other words, $R^1$ will be a substituent which will be polymerizable when the compound of formula (I) is polymerized into a polymer. For purposes of the present invention, $R^1$ can be any type of polymerizable group. This includes:

(1) Any unit with a double bond and is given by the following formula:

where $R^6$ is a hydrogen; an alkyl group with up to 25 carbons; an olefin group with up to 25 carbons; and $R^7$ is a hydrogen; a substituted or unsubstituted alkyl with up to 25 carbons; a substituted or unsubstituted aryl with up to 25 carbons; a halogen; a substituted or unsubstituted carboxylic group with up to 25 carbons; a substituted or unsubstituted amide group with up to 25 carbons; a cyanate; isocyanate; or a thiocyanate. In this unit, the substituents $R^6$ or $R^7$, preferably $R^7$ bond to $L^1$.

(2) Cyclic monomers which polymerize either through a double bond within the ring or by ring opening polymerization (ROMP). These include rings with three to eight members and the atoms within the ring are substituted and unsubstituted carbons, carbonyl, oxygen, substituted or unsubstituted phosphorus, or substituted or unsubstituted amides. The total number of carbons can be up to 40.

(3) Monomers with coreactive functional groups which can include the following:

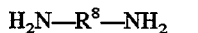
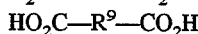
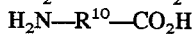
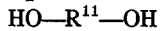
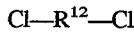
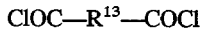

where $R^8$, $R^9$, $R^{10}$, $R^{11}$, $R^{12}$ and $R^{13}$ are independently selected from a substituted or unsubstituted alkyl with up to 25 carbons; a substituted or unsubstituted aryl with up to 25 carbons; a substituted or unsubstituted silane with up to 25 carbons; a substituted or unsubstituted nitrogen heterocycle with up to 25 carbons. In addition, $R^8$ can also be carbonyl. With these coreactive functional groups, the R groups (i.e., $R^8$ through $R^{13}$) bond to $L^1$.

Preferably, $R^1$ is an acrylate or methacrylate group.

$R^2$ and $R^3$ which can be the same or different is a substituted or unsubstituted alkyl of up to 15 carbons; a substituted or unsubstituted aryl having up to 30 carbons; a substituted alkoxy or thioalkyl of up to 15 carbons; a substituted or unsubstituted aryloxy or thioaryl having up to 20 carbons; oxygen or sulfur containing heterocycle with up to 25 carbons; where L=N, the group can also consist of substituted and unsubstituted amines, amides, and nitrogen heterocycles (e.g., pyridine) with up to 25 carbons.

$R^2$ and $R^3$ can alternatively interconnect to form a chelating ligand such as catechol. The partial structure would be as follows:

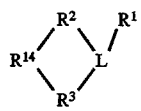

Preferably, $R^2$ and $R^3$ are alkyl or alkoxy groups of up to 15 carbons; or aryl or aryloxy groups of up to 25 carbons.

$R^{14}$ is an alkyl group of up to 6 carbons or represents a bond between $R^2$ and $R^3$, and preferably is a bond between $R^2$ and $R^3$.

$R^4$ is an anionic ligand. Examples of anionic ligands include, but are not limited to, a halogen, a cyanate, an isocyanate, a thiocyanate, an alkyl group that preferably does not contain an α- or β-hydrogen capable of undergoing elimination, a substituted or unsubstituted thioalkyl having up to 15 carbons; a substituted or unsubstituted thioaryl having up to 25 carbons; a sulfur containing heterocycle with up to 25 carbons; a substituted or unsubstituted aryloxide with up to 25 carbons; a substituted or unsubstituted alkoxide with up to 15 carbons; an oxygen containing heterocycle with up to 25 carbons; a substituted or unsubstituted cyclopentadienyl with up to 30 carbons; and an acetylacetonate with optional substitution of at least one of any of the hydrogens on any of the carbons therein with a halogen. When x is 2 or higher, $R^4$ can be the same or different.

Preferably, $R^4$ is a halogen, a cyanate, an isocyanate, or a thiocyanate.

$L^2$, when it exists, is a neutral ligand. For example, $L^2$ can be the same or different when [n−(x+m)] is two or greater. $L^2$ can be a trivalent phosphorus, trivalent arsenic, trivalent antimony compound or a divalent sulfur or divalent selenium or a divalent tellurium compound when bonded to either three (for trivalent compounds) or two (for divalent compounds) substituents (excluding the bond to M) which can be the same or different. These divalent or trivalent compounds, for example, can have substituents such as a halogen, a substituted or unsubstituted aryloxy or alkyloxy of up to 25 carbons, a substituted or unsubstituted alkyl, a substituted or unsubstituted aryl.

Alternatively, $L^2$ is a substituted or unsubstituted aryl or alkyl isocyanide; a carbonyl or carbon monoxide; a thiocarbonyl or carbon monosulfide; a nitrosyl; a substituted or unsubstituted amine; a nitrile with a substituted or unsubstituted alkyl or aryl; a coordinating solvent such as cyclic or linear ethers which include tetrahydrofuran (THF); a substituted or unsubstituted unsaturated alkyl or aryl which bonds to the M mainly through a π-bond.

When n−(x+m) is greater than 0 (i.e., 1 or higher), $L^2$ substituents will be attached to M due to the additional coordination sites of M. When there is more than one $L^2$ substituent, each $L^2$ substituent can be the same or different or chelating (i.e., interconnected). For instance, when M is chromium (III), n is six, x is three, m is one, and n−(x+m) is two. There would be two $L^2$ substituents which could both be, e.g., an amine or one $L^2$ substituent could be an amine element and the other $L^2$ substituent could be phosphine.

A preferred formula of formula (I) is formula (II):

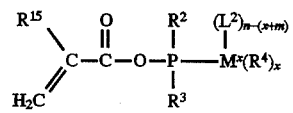

wherein $R^{15}$ represents a hydrogen or a linear alkyl group of up to 6 carbons.

A most preferred compound has the following formula:

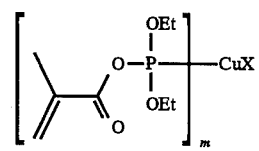

In this formula, M is Cu(I) metal which has biocidic effects in seawater and X is Cl, SCN, or SPh (thiophenyl). When X is Cl, m=1; when X is SCN, m=2; and when X is SPh, m=3. $L^1$ is P which forms the phosphite portion. This phosphite portion maintains the +1 oxidation state of the Cu and hydrolyzes to an inorganic phosphate. The acrylate portion of the compound is retained as the site for free-radical polymerization. When released, the phosphite portion further increases the acidity (i.e., lowers the pH) near the polymer surface. Having a lower pH near the polymer surface creates an undesirable environment to marine life, e.g., barnacles. The above compound can also couple electrochemically with $Cu_2O$ where the two Cu(+1) species convert to a Cu(O) and a Cu(+2) to provide a more effective release of Cu.

For purposes of the present invention, the following definitions are applicable to the terms as used in the present application.

An unsubstituted aryl group is defined to include at least one benzene ring, whether fused or not. "Fused" means two or more aromatic benzene rings share at least one carbon atom, such as for example in the case of biphenyl or naphthyl groups.

A substituted aryl group is defined to include the addition to one or more aryl ring carbons: at least one nitrogen-containing ligand, such as for example an azide, imine, ketimine, amine, amide, or imide; at least one oxygen-containing ligand, such as for example an alcohol, ether, ester, ketone, aldehyde, anhydride or organic acid such as carboxylic; at least one sulfur-containing ligand such as for example, a thiol, sulfide, disulfide, sulfone, sulfoxide, sulfonic ester, or sulfonic acid; substituted and unsubstituted alkyl groups such as defined in this application.

With respect to substituted and unsubstituted aryl groups, this is intended to also include methyl, ethyl or other alkyl substitutions including halogen substitutions and acyl halide carboxylic substitutions that are initiated by Friedel Crafts type catalysts. In other words any electrophilic or nucleophilic type reaction between an aryl and some substituent which leads to a product is intended to be covered as part of the substituted aryl group. Examples of such substituted aryl groups are: 2,4,6-trimethyl styrene; alpha-methyl styrene; m-bromo-styrene; and m-methyl-styrene.

Unsubstituted alkyl groups, whether saturated or unsaturated, and cyclic, branched, or unbranched are intended to include primarily compounds consisting essentially of only carbon and hydrogen. Examples of such materials include ones that satisfy the formula $C_yH_{2y+1}$ or $C_yH_{2y-1}$ where y can vary, e.g., from 1 to 20. y is at least 3 for cyclic alkanes, and y is at least 4 for branched cyclic alkanes.

Substituted alkyl groups, whether saturated or unsaturated and cyclic, branched, or unbranched, include materials that result from replacing one or more hydrogens of an unsubstituted "alkyl group" as defined herein with: at least one halogen, such as fluorine, chlorine, bromine, or iodine; at least one oxygen, nitrogen or sulfur, wherein the oxygen optionally has at least one additional carbon, nitrogen, or sulfur attached to it; the nitrogen optionally has at least one additional carbon, nitrogen, or sulfur attached to it; and the sulfur optionally has at least one additional carbon, nitrogen, or sulfur attached to it. Examples of substituted alkyls include such compounds as amines, alcohols, acids, esters, ketones, sulfides, sulfones, sulfoxides, isocyanates, cyanates, thiocyanates, nitriles, and nitrosones.

With regard to the preparation of the above-described compounds of formula (I), there are a variety of methods which can be used.

Generally, a compound having the formula (III)

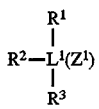

is reacted with a compound having the formula (IV)

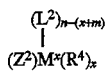

$L^1$, $R^1$, $R^2$, and $R^3$, in formula (III) and M, $L^2$, $R^4$, n, m, and x in formula (IV) have the same meaning as in formula (I) described above. $Z^1$ represents a pair of electrons on $L^1$ or a functional group (i.e., leaving group). Generally, $Z^1$ is any functional group which is replaceable by the available bond site from

Examples of functional groups encompassed by $Z^1$ include —OH, and halides. $Z^1$ will generally represent a pair of available electrons on $L^1$ when $L^1$ is nitrogen, phosphorous, arsenic, antimony, or bismuth. When $L^1$ is not a Group 15 element of the Periodic Table, such as sulfur or silicon, $Z^1$ can be a functional group such as —OH or a halide.

Compounds of formula (III) are generally commercially available from such sources as Aldrich Chemical Co.

Specific examples as well as the preparation of compounds of formula (III) wherein $L^1$ is phosphorous are described in Pudovik et al., Chemical Abstract, Vol. 63, 1965 (p. 13420) with regard to its discussion of phosphites. This reference is specifically incorporated herein by reference.

With respect to the compounds of formula (IV), $Z^2$ represents an empty orbital which has the proper orientation to accept the pair of electrons ($Z^1$) to form a L1—M bond. In addition, $Z^2$ can be a functional group which can react with $Z^1$ to form an independent $Z^1Z^2$ molecule and $L^1$-M bond. An example of such a functional group (i.e., leaving group) is a hydride group or a halide group. In such a case, the $Z^2$ functional group will bond with the $Z^1$ leaving group to form a compound and the compound of formula (I) will be formed by the open bond site in $L^1$ and the open bond site in $M^x$.

Furthermore, $Z^1$ can alternatively represent a pair of electrons, while $Z^2$ represents a labile ligand group such as acetonitrile. In such a case, the acetonitrile is stable by itself and upon breaking off from M, a bond forms between $L^1$ and $M^x$. $Z^2$ can also represent an empty orbital position on M that can accept electrons from $L^1$ when $Z^1$ represents a pair of electrons. One example of such a situation is when M is Cu(I) and $L^2$ is Cl.

Examples of compounds of formula (IV) include, but are not limited to, CuCl, CuSCN, $ZnCl_2$. Compounds of this type are generally commercially available from such sources a Strem Chemical Co. and Aldrich Chemical Co.

In view of the above, the description set forth below provides a more detailed preparation of preferred compounds of formula (I) of the present invention.

Preparation of the compounds described below generally follows a three-step synthesis. First, sodium acrylate or methacrylate is synthesized from the reaction of acrylic or methacrylic acid with sodium hydroxide. For example, the reaction scheme below shows a reaction of methacrylic acid with sodium hydroxide.

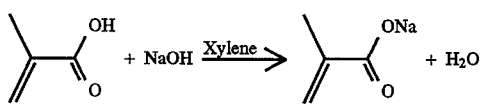

The sodium acrylate or sodium methacrylate, in turn, is reacted with chlorodiethylphosphite to give acrylodiethylphosphite or methacryiodiethylphosphite. For example, the reaction scheme below shows such a reaction for methacrylodiethylphosphite.

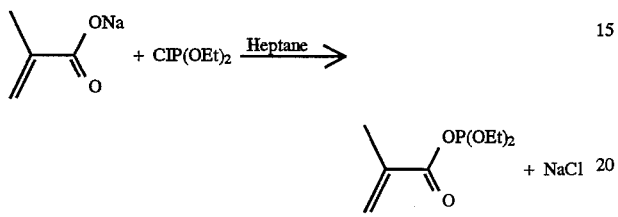

The acrylodiethylphosphite or methacrylodiethytphosphite, in turn and preferably in situ, is reacted with CuX (X=Cl, SCN, SPh (thiophenyl)) to form Cu acrylodiethylphosphite or methacrylodiethylphosphite. For example, the reaction scheme below shows such a reaction for CuX and methacrylodiethylphosphite.

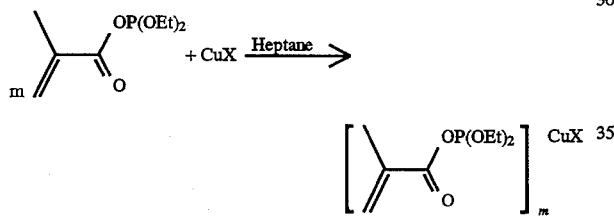

Both of these phosphorous containing compounds are abbreviated herein as the chemical symbol of the metal, here copper, followed by "P" and the word "monomer". Hence copper acrylophosphite is abbreviated as "PCuX monomer" and the corresponding zinc metal monomer as "PZnX monomer". A synthesis is described for CuCl, but the identical reactions apply for the preparation of CuSCN and CuSPh as well as other metals encompassed by M.

The presence of unreacted acrylic or methacrylic acid, water, or CuX can lead to undesirable side reactions. Accordingly, the sodium acrylate or methacrylate should be washed thoroughly to remove any unreacted acrylic or methacrylic acid. The remaining precipitate should then be dried (e.g., by means of a vacuum pump or a water-xylene azeotrope where the temperature is preferably maintained under about 35° C. and a vacuum is applied simultaneously). The presence of water results in the undesired hydrolysis of the acrylodiethylphosphite or methacrylodiethylphosphite to a phosphate, releasing the acrylate.

Acrylate or methacrylate groups in the presence of appended phosphites of Cu are predisposed to self polymerization. Hence, a cooling bath and dilution with more solvent are recommended. A solution temperature of less than about 15° C. is recommended, but at temperatures lower than about 5° C., incomplete phosphite incorporation may be observed and should be avoided.

The series of PCuX monomers is limited by the number of stable CuX compounds. The PCuX monomer is typically a colorless or light yellow viscous liquid that should polymerize under the influence of heat or light.

The number of phosphites per CuX unit varies, depending on X. For example, in the case of CuCl there is only one phosphite per CuCl. In the case of CuSCN, there are two phosphites per CuSCN, and in the case of CuSPh there are three phosphites per CuSPh unit.

UV photolysis of the PCuCl monomer gives a green white solid and two phosphates. In other words, Cu was released. The presence of chlorodiethylphosphate indicates that a homolytic cleavage of the Cu—$L^1$ (e.g., Cu—P) bond has taken place, followed by a rearrangement to release the phosphate. (See Rxn (a).) The same decomposition reactions were observed for PCuSCN monomer and PCuSPh monomer. (See Rxn (b) and (c).)

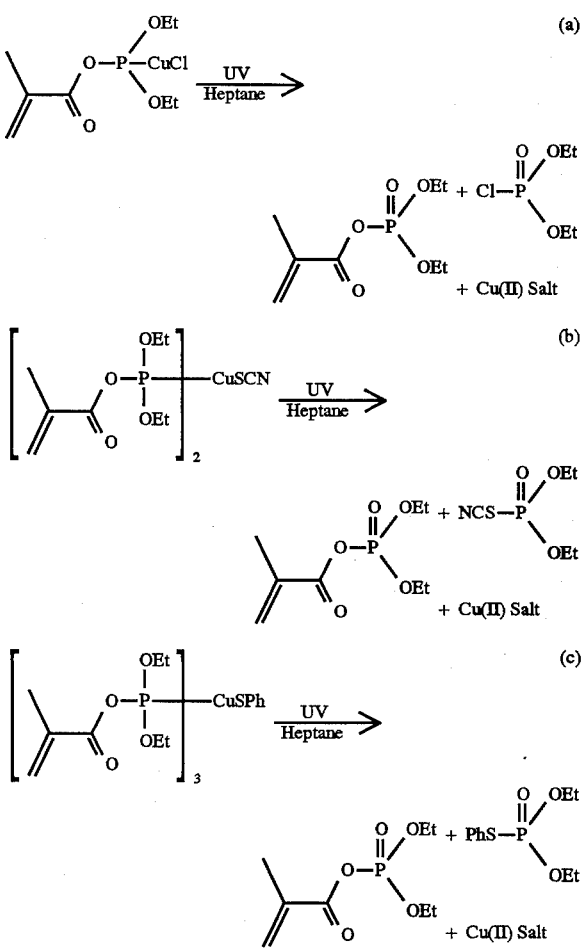

The electrochemical behavior of the PCuX monomers were determined using cyclic voltammetry. The electrochemical cell contained 10 mL of the PCuX monomer in $1 \times 10^3$M saturated $CH_2Cl_2$ solution of tetrabutylammonium hexafluorophosphate. The reference electrode was a saturated calomel electrode (SCE), the working electrode was carbon, and the auxiliary electrode was Pt. The procedure followed was described in the CV-27 Cyclic Voltammograph manual. Electrochemical studies of the monomers gave the following results:

|  | Reduction Potential | Oxidation Potential |
|---|---|---|
| [H$_2$C=C(CH$_3$)C(O)O](EtO)$_2$PCuCl | −1.00 eV | 1.375 eV |
| {[H$_2$C=C(CH$_3$)C(O)O](EtO)$_2$P}$_3$CuSPh | −1.350 eV | 0.935 eV |
| [H$_2$C=C(CH$_3$)C(O)O](EtO)$_2$PCuSBu$^t$ | −1.355 eV | 0.875 eV |

The electrochemical results are relevant because they demonstrate that the Cu compounds can couple with another Cu(+1) compound, Cu$_2$O, to give Cu(O) and Cu(+2) complexes (reaction (d)). This can aid in the controlled release of both Cu species.

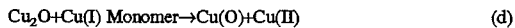

Once the compound of formula (I) is formed, as discussed above, this compound can then be polymerized with one or more other monomers to form a polymer. Preferably, a methacrylate monomer and a film softening monomer, such as an acrylate monomer, are polymerized with a compound of formula (I) to form a terpolymer. Preferably, the compounds of formula (I) with one or more other monomers, such as the film softening monomer and methacrylate monomer, are polymerized by free radical polymerization except in the case where M is Cu(II). Additionally, compounds of formula (I) with one or more monomers, such as the film softening monomer and methacrylate monomer, can also be polymerized by condensation polymerization. A solvent should be used such that the polymer remains soluble in the solvent. Generally, ketone-based solvents are preferred and methyl ethyl ketone is most preferred. The polymerization reaction is preferably initiated by a free radical initiator. Once polymerized, the polymer may have the following repeating unit:

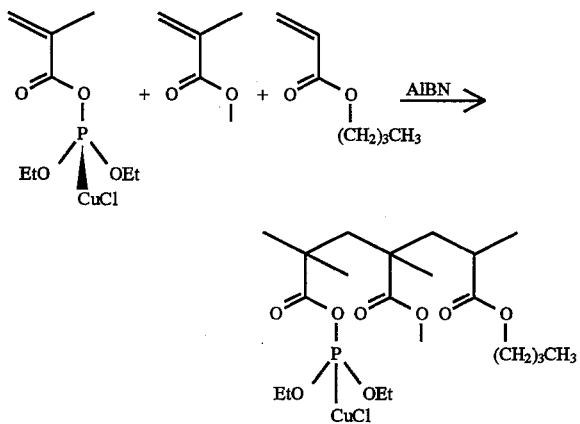

However, the monomers are incorporated randomly into the polymer.

Examples of film softening monomers include, but are not limited to substituted and unsubstituted acrylate monomers such as: methyl acrylate; ethyl acrylate; butyl acrylate; ethyl methacrylate; butyl methacrylate; isobutyl methacrylate; isooctyl acrylate; 2-ethylhexyl methacrylate; nonyl acrytate; nonyl methacrylate; lauryl methacrylate; stearyl methacrylate; dimethylaminoethyl acrylate; dimethylaminoethyl methacrylate; trifluoroethyl methacrylate; 2-methoxyethyl acrylate; 2-ethoxyethyl methacrylate; 2-ethylhexyl acrylate; and t-butylaminoethyl methacrylate.

In particular, it has been discovered that it is possible by use of certain free radical initiators to polymerize the unsaturation of the acrylate component of the above material. However, polymerizing such monomers by a free radical initiator such as those that use hydrogen peroxide or an organic based peroxide, such as a carboxylic acid based benzoyl peroxide, will usually lead to oxidation of copper (I) to copper (II) and destruction of the copper-containing monomer.

Preferably, the free radical initiators suitable especially for copper-containing monomers of this invention include azo type compounds, for example, azonitriles; azoamidines; azo moieties substituted with alkyls; and azo moieties substituted at the alpha carbon with combinations of one or more of the following: alcohols, esters, nitriles, amides, aminoalcohol, and substituted amines and amides thereof.

Examples of commercially available azonitriles sold by Wako Pure Chemical Industries Ltd. are: Azonitrile Compounds; 2.2'-Azobis(4-methoxy-2.4-dimethylvalero-nitrile), 2.2'-Azobis(2.4-dimethylvaleronitrile), 2.2'-Azobis(2-methylpropionitrile), (2.2'-Azobisisobutyronitrile), 2.2'-Azobis(2-methylbutyronitrile), 1.1'-Azobis(cyclohexane-1-carbonitrile), 1-[(1-Cyano-1-methylethyl)azo]formamide (2-(Carbamoylazo)isobutyronitrile), 2-Phenylazo-4-methoxy-2.4-dimethyl-valeronitrile, Azoamidine Compounds: 2.2'-Azobis(2-methyl-N-phenylpropion-amidine) dihydrochloride, (2.2'-Azobis(2-(N-phenylamidino)propane)dihydrochloride, 2.2'-Azobis[N-(4-chlorophenyl)-2-methyipropionamidine]dihyrochloride, (2.2'-Azobis 2-[N-(4-chlorophenyl)amidino] propanel dihydrochloride), 2.2'-Azobis[N-(4-hydroxyphenyl)-2-methylpropionamidine] dihydrochloride) (2.2'-Azobis 2-[N-(4-hydroxyphenyl) amidino]propane dihydrochloride, 2.2-Azobis[2-methyl-N-(phenylmethyl)-propionamidine]dihydrochloride, 2.2'-Azobis[2-(N-benzylamidino)propane]dihydrochloride, 2.2'-Azobis[2-methyl-N-(2-propenyl) propionamidine] dihydrochloride, 2.2'-Azobis [2-(N-allylamidino)propane] dihydrochloride, 2.2'-Azobis(2-methylpropionamidine) dihydrochloride, (2.2'-Azobis(2-amidinopropane) dihydrochloride, 2.2'-Azobis[N-(2-hydroxyethyl)-2-methylpropionamidine]dihydrochloride, (2.2'-Azobis 2-N-2-hydroxyethyl)amidino]propane dihydrochloride, Azoamide Compounds: 2.2'-Azobis 2-methyl-N-[1,1-bis (hydroxymethyl)-1-hydroxyethyl]propionamide, 2.2'-Azobis 2-methyl-N-[1.1-bis(hydroxymethyl)ethyl] propionamide, 2.2'-Azobis[2-methyl-N-(2-hydroxyethyl)-propionamide], 2.2'-Azobis (2-methylpropionamide) dihydrate, (2.2'-Azobis(isobutyramide)dihydrate), Alkylazo Compounds: 2.2'-Azobis(2,4,4-trimethylpentane) (Azoditert-octane), 2.2'-Azobis(2-methylpropane) (Azodi-tert-butane) and for azo moieties substituted at the alpha carbon with combinations of one or more of the following: alcohols, esters, nitriles, amides, aminoalcohol, and substituted amines and amides thereof. Other examples include Dimethyl, 2.2'-azobis(2-methylpropionate) (Dimethyl 2.2'-azobisisobutyrate), 4.4'-Azobis(4-cyanovaleric acid), (4.4'-Azobis(4-cyanopentanoic acid)), 2.2'-Azobis[2-(hydroxymethyl)propionitrile]

Organic based peroxide initiators, while generally not suitable for poiymerizing or copolymerizing copper containing monomers of this invention, are however suitable for polymerizing other metals within the scope of this invention when they are used in place of copper. Examples of these alternative initiators are: organosulfonyl peroxides; dialkyl or diaryl or alkyl aryl peroxides; diacyl peroxides; ketone peroxides; peroxyketais; peroxydicarbonates; peroxycarbonates; and peroxyesters.

Examples of these materials are available commercially from Elf Atochem North America, Inc. under the trade name LUCIDOL. Specific chemical examples of some of these materials are: Diacyl peroxides; 2,4-Dichloro Benzoyt Peroxide, Diisononanoyl Peroxide, Decanoyl Peroxide, Lauroyl Peroxide, Succinic Acid Peroxide, Acetyl Peroxide, Benzyol Peroxide, Ketone Peroxide; 2,4-Pentanedione Peroxide, Peroxydicarbonates; Di(n-propyl) Peroxydicarbonate, Di(sec-butyl) peroxydicarbonate, Di(2-ethylhexyl) peroxydicarbonate, Di(2-phenoxyethyl) Peroxydicarbonate, Peroxyesters; α-cumylperoxy Neodecanoate, α-cumylperoxy Pivalate, t-Butylperoxy Neodecanoate, t-Butylperoxypivalate, 2,5-Dimethyl 2,5-di (2-ethylhexanoyl peroxy)hexane, t-Butylperoxy-2-ethylhexanoate, t-Butylperoxyiosbutyrate, t-Butylperoxymaleic acid, 2,5-Dimethyl-2,5-di (benzyolperoxy) hexane, t-Butylperoxy Acetate, t-Butylperoxy Benzoate, Di-t-Butyl diperoxyphthalate, t-Amyl peroxy pivalate, Dialkyl Peroxides, Dicumyl Peroxide, 2,5-Dimethyl-2,5-di(t-butylperoxy)hexane, Di-t-Butyl Peroxide, 2,5-Dimethyl-2,5-di(t-butylperoxy)hexyne-3, Hydroperoxides; 2,5-Dihydroperoxy-2,5-dimethylhexane, t-Butyl Hydroperoxide, Peroxyketals; 1,1-Di(t-butylperoxy) 3,3,5-trimethyl cyclohexane, 1,1-Di(t-butyl-peroxy) cyclohexane, 2, 2-Di(t-butylperoxy)butane, Ethyl-3,3-Di(t-butylperoxy)butyrate.

In addition, one or more of the following substituted or unsubstituted monomers can be polymerized with a monomer of formula (I): acrylates; acroleins; acrylonitriles; acrylamides; acryloyl halides; allyls; butadienes; citraconimide; diallyls; isoprenes; iraconic acids; itaconamates; itaconimides; maleic alkylates; maleic anhydrides; maleimides; methacrylamides; alkyl methacrylates; methacrylic acids or anhydrides; oxazolines; pyrrolidones; styrenes; vinyls; and vinylidene halides. Some typical examples of some of these are: with respect to acrylates: alpha-acetoxy ethyl acrylate; alpha-chloro methyl acrylate; alpha-trifluoromethyl methyl acrylate; benzyl acrylate; ethyl acrylate; ferrocenylmethyl acrylate; isobutyl acrylate; and phenyl acrylate; with respect to butadiene, 2,3-dichloro butadiene; 2-chloro butadiene; Acrylamide; α-fluoroacrylamide, N-octadecyl-acrylamide, Acrylate; methyl-α-chloro acrylate, methyl, α-fluoromethyl-acrylate, benzyl acrylate, ethyl acrylate, ferrocenylmethyl acrylate, isobutyl acrylate, phenyl acrylate, Acrylic acid; α-bromo-acrylic acid, Acrylonitrile; α-trifluoromethyl-acrylonitrile, Allyl; alcohol allyl, Butadiene; 2,3-dichloro-butadiene, 2-chloro-butadiene, Citraconimide; N-benzyl-citraconimide, N-butyl-citraconimide, N-isobutylcitraconimide, Diallyl; melamine diallyl, phthalate diallyl, Diallylcyanamide; Isoprene; 3-acetoxy-isoprene, Isopropenyl acetate; Itaconamate N-phenyl-ethyl; Itaconate dibutyl; Iraconic acid; Itaconimide, N-benzyl; Maleimide; N-(4-hydroxyphenyl)-maleimide, N-benzyl-maleimide, N-butyl-maleimide, N-phenyl-maleimide, Methacrylamide; N-methoxymethyl-methacrylamide, N-phenyl-methacrylamide, Alkylmethacrylates; benzyl alkylmethacrylate, chloromethyl alkylmethacrylate, cyanomethyl alkylmethacrylate, glycidyl alkylmethacrylate, 2-hydroxyethyl alkylmethacrylate, 2-hydroxypropyl alkylmethacrylate, 2-phenethyl alkylmethacrylate, Methacrylic acid; anhydride methacryiic, Oxazolidone; N-vinyl oxazolidone, Pyrrotidone; α-methylene-N-methyl-pyrrolidoe, N-vinyl-pyrrolidone, 1-benzyl-3-methylene-5 methyl pyrrolidone, Styrene; α-methyl-styrene, 2,4,6-trimethyl-styrene, 2,5-dichloro-styrene, m-bromo-styrene, m-chloro-styrene, m-methyl-styrene, p-bromo-styrene, p-chloromethyl-styrene, p-N,N-dimehtylamino-styrene, Vinyl; acetate vinyl, benzoate vinyl, bromide vinyl, butyrate vinyl, chloride vinyl, ether vinyl, ethyl ether vinyl, ethyl ketone vinyl, ethyl oxalate vinyl, ethyl sulfide vinyl, ethyl sulfoxide vinyl, phenyl ketone vinyl, propionate vinyl, sulfone vinyl, vinylferrocene, vinylhydroquinone, dibenzoate vinylhydroquinone, Vinylidene; chloride vinylidene, cyanide vinylidene, Vinylisocyanate; Vinyltrimethylsilane.

The choice of the monomers is dependent on the properties required for each controlled release application. For example, polymers for marine antifoulant applications must give a flexible film with good mechanical integrity. Therefore, the monomer of formula (I) must be polymerized with a rubbery monomer for flexibility (e.g., butyl acrylate) and a hard monomer for good mechanical properties (e.g., methyl methacrylate).

Polymerization of the PCuCl and other transition metal monomers of this invention with methyl acrylate (MA), methyl methacrylate (MMA) and butyl acrylate (BA) in MEK gives a polymer solution with Mw of about 50,000 to about 60,000.

The polymer acts as a binder which is held in suspension by a solvent such as a ketone, preferably methylethyl ketone. Then, pigments, dyes, and other biocides are added in manners known to those skilled in the art. A description of such components and ways to add such components to form the paint is described in a technical book entitled *Marine Biodeterioration: An Interdisciplinary Study*, J. D. Costlaw and R. C. Tipper, Eds., Naval Institute Press, Annapolis, Md., 1984, incorporated herein by reference, with particular emphasis on the chapter titled "The Chemical and Physical Characterization of Marine Coatings Containing Organotin Antifoulants" by M. L. Good and C. P. Monaghan.

Once formed into a paint, the paint can be applied to a surface such as a hull, and upon application, the solvent (e.g., ketone) evaporates leaving the polymer with other ingredients. Preferably, the solvent that is used has a long alkyl chain which permits a slow evaporation of the solvent which assists in avoiding trapping of the solvent beneath the interior layers of the paint.

The preferred organometallic polymers made in accordance with this invention achieve the following:

1. The polymer is solvent soluble, for easy application.
2. The polymer solution provides a clear, hard film with enough flexibility to coat a ship's surface.
3. The film undergoes at least some surface hydrolysis to release a metal, to become a material that either dissolves or swells and is attritted or dissolved off to provide a fresh and new polymer layer that is preferably smooth to preserve a ship's fuel efficiency.

The polymers of the present invention are also capable of releasing in a controlled manner an active agent. Controlled release systems permit an active chemical agent (e.g. $Cu_2O$; Manganese ethylenebisdithiocarbamate (Maneb); Zinc dimethyldithiocarbamate (Ziram); 2(Cyclopropylamino)-4-isobutylamino-6-methylthio-S-triazine; N'(3,4-dichlorophenyl)-N,N-dimethyl urea (Diuron); Zinc ethylenebisdithiocarbamate (Zineb); N-(fluorodichloromethylthio) phthalimide Fluorofolpet); N,N-dimethyl-N'-phenyl-N'-(fluorodichloro-methylthiosulphamide (Dichlorofluanide, Euparen); Tetramethylthiuram disulfide (Thiram); Methylene bis(thiourea); 4-Butyl catechol; Captan; Zinc dimethyl dithiocarbamate; 2-Methylthio-4-t-butylamino-6-cyclopropylamino-s-triazine; 2,4,5,6-Tetrachloroisophthalonitrile; N,N-Dimethyl-N'-dichlorophenyl urea; Copper thiocyanate; 4,5-Dichloro-2-n-octyl-3(2H) isothiazolone; N-Fluorodichloromethylthio-phthalimide; N,N-Dimethyl-N'-phenyl-N'-fluorodichloromethylthio-sulfamide; 2-Pyridinethiol-1-oxide zinc salt; Tetramethyl thiuram disulfide; Copper-nickel (10%) solid solution alloy; 2,4,6-Trichlorophenyl maleimide; 2,3,5,6-Tetrachloro-4- methylsulfonyl pyridine; 3-Iodo-2-propenyl butyl carbamate; Diiodomethyl p-toluyl sulfone; Bis-(dimethyldithiocarbamoyl zinc)ethylene bis-dithiocarbamate; Pyridine triphenylboran; Zinc-2-pyridinethiol-N-oxide (Zinc Omadine) (Zinc salt of 1-hydroxy-2-pyridinethione); Tetrachloroisophthalonitrile (NuoCide 960s) (Chlorothalonil); 1-Methylthio-3-(t-butylamino)-5-(cyclopropylamino)-S-triazine (Irgarol 1051); 4,5-Dichloro-2-n-octyl-3-(2H)-isothiozolone/chloro-2-n-octyl-3-(2H)-isothiazolone 7/1 (Anti-Foulant 3-9211M); Isothiazolone, an organosulfur biocide (Rohm & Haas, Philadelphia)) to be transferred to a specified target at a rate and duration designed to accomplish an intended effect. These systems have found growing use in many areas, for example, in pharmaceuticals, catalysts, pesticides, and antifoulants. For purposes of the present invention, the basic components of a controlled release system include the active agent and the polymer matrix which regulates the active agent's release. The use of the polymer system is dependent on its properties and these can be tailor-made for each controlled release application. The controlled release system that is particularly useful with the compounds of the present invention are "erodable" systems. In particular, the active agent is blended so that it either dissolves in, is physically dispersed in, or is chemically bound to the polymer matrix. The polymer used is either soluble or degrades during use and the active agent is released by a combination of diffusion and liberation due to erosion. The metal containing polymer systems as described in this invention refer to a delivery system which will release an active agent through surface erosion due to an environmental agent such as water.

The main advantage of controlled release systems is that they allow much less of the active agent to be used more effectively over a given period of time. For example, pesticides or biocides can be released in a controlled manner fox an extended period of time. A particular example is the marine antifoulant controlled release systems of the present invention which have extended the lifetime of ship's coatings from two years to five years.

Furthermore, the present invention relates to metal complexes having the formula (II):

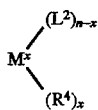

where the definitions of M, x, $L^2$, n, and $R^4$ are the same as in formula (I). Compounds of formula (II) can be used as additives to such compositions as paint formulations in order to prevent fouling on surfaces susceptible to fouling. Manners in which the metal complex is incorporated in compositions such as paint formulations as well as means to apply the composition to surfaces (e.g., ship hulls) are known to those skilled in the art.

In the examples set forth below, there is a comparison of the effectiveness of introducing copper into a polymer such as that disclosed above which initially does not contain copper.

To obtain optimal film forming properties the average molecular weight of polymers, measured in accordance with ASTM method number D 5296-92, made from monomers made and used in accordance with this invention are preferably in the range of about 5000 to 200,000; more preferably in the range of about 10,000 to 75,000.

Based on this description, and the specific examples that follow, one skilled in the art can generally follow the procedures described below in preparing all of the compounds of formula (I).

EXAMPLES

Monomer Syntheses

Example 1

Synthesis of $[H_2C=C(CH_3)C(O)O]P(OEt)_2$

Methacrylic acid in slight excess was reacted with NaOH in xylene to give Na acrylate and $H_2O$. The solid Na acrylate was collected and washed with xylene and heptane until methacrylic acid could not be detected and then any remaining traces of $H_2O$ were removed under vacuum. Table 1 sets forth the precise details of the synthesis.

TABLE 1

Sodium Acrylate Synthesis

| Materials | M.W. | Moles | Charged (g) |
|---|---|---|---|
| Methyacrylic Acid | 86.09 | 1.18 | 100 |
| Sodium Hydroxide | 40.00 | 1.125 | 45 |
| Xylene | 106.17 | | 650 |
| Xylene wash | | | 400 |
| Heptane Wash | | | 350 |
| Total Charge: | | | 1545 |

1. Charge 650 g xylene into a 3 L four-necked flask with xylene.
2. Degas xylene.
3. Charge 100 g methacrylic acid into the reaction flask.
4. Add 45 g sodium hydroxide in three equivalent over 3 h.
5. Stir for 2 days under nitrogen.
6. Collect the sodium acrylate in a Schlenk filter.
7. Wash the sodium acrylate three times with xylene (total: 400 g) and three times for heptane (total: 350 g).
8. Pump off residual solvents and water. Dry under vacuum for 2 days.

A dilute solution of Na acrylate with chlorodiethylphosphite in heptane was then reacted over several hours to give acrylodiethylphosphite and NaCl. The reaction was monitored to ensure that all of the chlorodiethylphosphite was consumed. A slight excess (1.15) of the Na acrylate was used. The NaCl was filtered off to give a heptane solution of acrylodiethylphosphite. This phosphite was reacted in situ with CuCl as discussed in Example 2 below. Table 2 sets forth the precise details of this synthesis.

The phosphite was characterized by: GC-MS (parent ion=206.10), IR spectroscopy [v(CO)=1708 $cm^{-1}$ and v(P—O)=1027 $cm^{-1}$), and $^{31}$P-NMR spectroscopy (134 ppm).

Example 2

Synthesis of $[H_2C=C(CH_3)C(O)O](EtO)_2PCuCl$

CuCl was added to the above heptane solution of acrylodiethylphosphite, which was cooled to 2°–5° C. A viscous purple layer separated out and was isolated as a purple oil. The viscous purple oil was stirred and resulted into a brown oil. The $[H_2C=C(CH_3)C(O)O](EtO)_2PCuCl$ complex thus formed, was washed with heptane. Unreacted CuCl was filtered off from the solution of the complex in methylethylketone. Table 2 also sets forth the precise details of this synthesis.

TABLE 2

CuCl Monomer Synthesis

| Materials | M.W. | Moles | Charged (g) |
|---|---|---|---|
| Sodium Acrylate | 108.08 | 139 | 15 |
| ClP(OEt)$_2$ | 156.55 | 124 | 19 |
| CuCl | 98.99 | 91 | 9 |
| Heptane | | | 200 |
| Heptane wash | | | 50 |
| Methylethylketone | | | 16 |
| Total Charge: | | | 309 |

1. Dry glassware in oven. Assemble glassware and dry further with heat gun.
2. Charge sodium acrylate into reaction flask under N$_2$.
3. Add 200 g dry heptane to reaction flask via cannula.
4. Maintain reaction solution at 2–5° C. (cold water bath).
5. Agitate the solution and syringe ClP(OEt)$_2$ dropwise. Keep the solution temperature at below 10° C.
6. Continue stirring for two hours. NOTE: Reaction is complete when no ClP(OEt)$_2$ is detected in the GC-MS spectrum.
7. Filter off the NaCl by product and cool reaction solution to †10° C.
8. Add CuCl to reaction solution over 1 h. Keep the solution temperature at 10–13° C. during CuCl addition. NOTE: The product is a purple oil which turns brown with continued stirring.
9. Syringe off the heptane layer.
10. Add 16 g of MEK and filter. NOTE: Characterize the CuCl monomer by $^1$H— and $^{31}$P-NMR spectroscopy.
11. Use the MEK solution of the CuCl monomer for the polymerization. IF the CuCl monomer will not be used immediately, store the solution in the freezer.

For CuSPh and CUSBu$^t$ Synthesis the procedure followed was similar to that given in ref. 1.

Elemental analyses disclosed that the mole ratio of P:Cu:Cl was 1:1:1. The NMR spectrum indicated that the phosphite was intact and bonded to the Cu. The peak had shifted upfield from 134 to 120 ppm and was broad due to coupling the phosphorus with $^{63}$Cu (abundance=69.1%) and $^{65}$Cu (abundance=30.9%), both of which had spins of 3/2. The IR spectrum gave a v(CO) peak at 1720 cm$^{-1}$ which had shifted from 1708 cm$^{-1}$.

Example 3

Synthesis of {[H$_2$C=C(CH$_3$)C(O)O] (EtO)$_2$P}2CuSCN

CuSCN was suspended in heptane and mixed with a heptane solution of [H$_2$C=C(CH$_3$)C(O)O]P(OEt)$_2$. The phosphite in slight (about 10%) excess was prepared in situ and reacted by stirring at room temperature for at least 12 hours. The resulting {[H$_2$C=C(CH$_3$)C(O)O](EtO)$_2$P}$_2$CuSCN was isolated as a filtered yellow oil.

The IR spectrum gave a v(CO) at 1723 cm$^{-1}$, a phosphite band at 1024 cm$^{-1}$ and a u(SCN) band at 2115 cm$^{-1}$.

Example 4

Synthesis of {[H$_2$C=C(CH$_3$)C(O)O] (EtO)$_2$P}$_3$CuSPh

CuSPh was prepared from a 1:2 molar mixture of Cu$_2$O and HSPh in dry ethanol. The mixture was heated to reflux until bright yellow precipitate CuSPh was formed and substantially all of the Cu$_2$O had reacted to the phenyl thiol of copper. The precipitate was washed with ethanol and xylene.

The CuSPh compound was then reacted with [H$_2$C=C(CH$_3$)C(O)O]P(OEt)$_2$ in a heptane solvent. A yellow solution resulted which was susceptible to light decomposition with time. The IR spectrum gave multiple peaks due to v(CO) at 1791, 1733, and 1717 cm$^{-1}$.

Example 5

CuCl-MMA-BA Terpolymer Synthesis

Table 3 sets forth details of the polymerization of CuCl monomer with methyl methacrylate (MMA) and butyl acrylate (BA). The composition of the solids in the starting solution was 27 mol % CuCl monomer, 65 mol % MMA, and 8 mol % butyl acrylate (BA). The final component of the solution was 80 wt % MEK. The BA was added to give the polymer more flexibility, thus offsetting the rigidity of the MMA component.

TABLE 3

Polymerization of CuCl Monomer with MMA and BA

| Materials | M.W. (g/mol) | Moles | Charged (g) |
|---|---|---|---|
| CuCl monomer | 305.2 | 0.085 | 26 |
| Methyl methacrylate (MMA) | 100.12 | 0.205 | 20.5 |
| Butyl Acrylate (BA) | 128.17 | 0.025 | 3.2 |
| AIBN | 164.21 | 0.006 | 1 |
| Methylethylketone (MEK) | 72.11 | 0.006 | 199 |
| Total Charge: | | | 249.7 |

1. Charge 20.5 g MMA, 3.2 g BA, and 175 g MEK into a 500 mL, four-neck reaction flask.
2. Degas the solution for 30 minutes.
3. Place the flask in a heated mantled air-jack.
4. Heat flask to 80° C. NOTE: A vigorous agitation is necessary to minimize insoluble solids formation.
5. Add 10 mL MEK solution of AIBN via a syringe pump over 4 h. At the same time, add solution of 20 mL MEK and CuCl monomer via a syringe pump over 3 h.
6. Continue heating to 80° C. for an additional 10 h.
7. Retain the soluble ortion of the polymer solution NOTE: Characterize for LOD (loss on dissolution) and by $^1$H— and $^{31}$P-NMR spectroscopy.

Example 6

Erosion Studies

The film forming properties have been demonstrated using the terpolymers of the PCuCl monomer with methyl methacrylate and butyl acrylate. A polymer solution synthesized using the method given in Example 5 was used. The MEK solution of the polymer was placed on sanded fiberglass panels and the MEK was allowed to evaporate at ambient temperatures over three days. A hard film resulted.

The erosion capability of the polymer binder was tested in artificial seawater. The polymer solution was formulated with cuprous oxide and Bentone 27 in the following weight ratios:

| Ingredient | Pts/wt |
| --- | --- |
| Polymer Solids | 10.00 |
| Cuprous oxide | 20.00 |
| Bentone 27 | 1.0 |

The above mixture was poured into a tin and mixed using a paint shaker. Cuprous oxide is a cotoxicant that is typically added to most antifoulant formulations. The low solids content of the polymer solution made it necessary to add a thickener (Bentone 27) in order to prevent the cuprous oxide from settling out of the solution. This pigmented solution was placed on a sanded fiberglass panel and allowed to dry over 3 days. The panels were placed in a circulating tank of artificial seawater and were monitored over time. The following results were observed.

1. Small green spots were observed after one day of immersion and disappeared with time. A uniform film was obtained afterward and surface erosion was observed.
2. After two weeks of immersion testing, the panel was placed in a beaker of moving artificial seawater for three days. Testing of the water solution for % Cu release indicated that it was comparable to the organotin control (1.84 ppm vs. 1.11 ppm).
3. The film had good integrity and good adhesion to the panel.

Several different factors were determined as a result of this polymerization of the CuCl monomer:

1. The initiator generally required was an AIBN (2,2'-azobis(isobutyronitrile)) type compound. Benzoyl peroxide tended to oxidize the Cu(I) to Cu(II), i.e., the solution turned from colorless to a dark purple. A minimum of ~0.5 mol % of AIBN, based upon the total number of moles of all monomers present, is generally required for polymerization to be observed.
2. Preferably, the reaction temperature is preferably about 80° C.
3. The addition rate of both AIBN and CuCl are important and preferably are added separately at about the same rate and time to the reaction medium that contains a ketone solvent, such as acetone or methyl ethyl ketone, and a comohomer, MMA and/or BA. Addition rates that take in excess of several hours are generally required depending upon the comonomer. The quantity of AIBN used is between 0.5 and 2.0 mole percent, as based upon the total number of moles of all monomers presents. Sometimes an insoluble solid will form. An NMR spectra of a portion of the insoluble solid revealed that a polymer had formed.

Specific compositions, methods, or embodiments discussed herein are intended to be only illustrative of the claimed invention. Variations of any of these would be apparent to one skilled in the art based upon the teachings contained herein and are intended to be within the scope of the present invention. For example, only copper containing polymers are expressly discussed in the examples. Others are made substantially the same way by substituting a different metal in place of all or a portion of the copper in the syntheses discussed.

For example, it is within the intended scope of this invention to include known antifoulant materials, such as $Cu_2O$ or CuSCN, within the resin compositions as useful additives provided that they are compatible or can be made so with the resin matrix.

For still another example, use of the fact that acrylic-phosphite esters containing copper (I) as a coordinated species can be hydrolyzed and oxidized to phosphate esters and then phosphoric acid functional groups, as a method for controlling pH and rates of hydrolysis depending upon the length of the organic component of the phosphate ester. Additionally, controlling the amount of hydrolysis after the polymer has been formed and before incorporating the material into a final coating affords a useful route for controlling availability of different forms of antifoulant metal, or changing the polarity and/or hydrolyric properties of the polymer.

Other embodiments of the present invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound of formula (I)

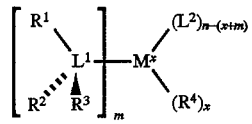

wherein $L^1$ is an element of Groups 13–16 of the Periodic Table;

$L^2$ is a neutral ligand;

M is a transition element or a metal element of Groups 13–16 of the Periodic Table;

n represents the number of coordination sites of M;

x represents the oxidation state of M, $R^1$ is a polymerizable group;

$R^2$ and $R^3$ are independently selected from the group consisting of an alkyl of up to 15 carbons; an aryl of up to 30 carbons; an alkoxy or thioalkyl of up to 15 carbons; an aryloxy or thioaryl of up to 20 carbons; an oxygen or sulfur containing heterocycle of up to 25 carbons; an amine; an amide; and a nitrogen heterocycle of up to 25 carbons with the proviso that L is not N; or $R^2$ and $R^3$ having the same definitions as above, interconnect to form a chelating ligand;

$R^4$ is an anionic ligand and when x is greater than 1, each $R^4$ is the same or different; and m is 1, with the proviso that m is 2 when M is Cu, x is 1, $L^1$ is phosphorus, $L^2$ is not present and $R^4$ is cyanate; and m is 3 when M is Cu, x is 1, $L^1$ is phosphorus, $L^2$ is not present, and $R^4$ is a thioalkyl having up to 15 carbons or a thioaryl having up to 25 carbons; and also with the proviso that when M is Rh, $R^1$ is a polymerizable group having a ($=CH_2$) group.

2. The compound of claim 1, wherein $R^4$ is selected from the group consisting of a halogen, a cyanate, an isocyanate, a thiocyanate, a thioalkyl of up to 15 carbons; a thioaryl of up to 25 carbons; a sulfur containing heterocycle of up to 25 carbons; an alkoxide of up to 15 carbons; an aryloxide of up to 25 carbons; an oxygen containing heterocycle of up to 25 carbons; a cyclopentadienyl of up to 30 carbons; and an acetylacetonate optionally substituted by a halogen.

3. The compound of claim 1, wherein $R^1$ has the formula

wherein $R^6$ is a hydrogen; an alkyl of up to 25 carbons; an olefin of up to 25 carbons; and $R^7$ is a hydrogen; an alkyl of up to 25 carbons; an aryl of up to 25 carbons; a halogen; a carboxylic group of up to 25 carbons; an amide group of up to 25 carbons; a cyanate; an isocyanate; or a thiocyanate.

4. The compound of claim 1, wherein $R^1$ is a cyclic monomer polymerizable through ring opening polymerization or through a double bond within the ring.

5. The compound of claim 4, wherein the cyclic monomer has three to eight members selected from the group consisting of a carbon; a carbonyl; an oxygen; a phosphorus; and an amide; with the proviso that the total number of carbons in the cyclic monomer does not exceed 40.

6. The compound of claim 1, wherein $R^1$ is a monomer with at least one coreactive functional group.

7. The compound of claim 6, wherein the monomer with at least one coreactive functional group has one of the following formulas:

$H_2N—R^8—NH_2$;
$HO_2C—R^9—CO_2H$;
$H_2N—R^{10}—CO_2H$;
$HO—R^{11}—OH$;
$Cl—R^{12}—Cl$; or
$ClOC—R^{13}—COCl$;

wherein $R^9$, $R^{10}$, $R^{11}$, $R^{12}$, and $R^{13}$ are independently selected from the group consisting of an alkyl of up 25 carbons; an aryl of up to 25 carbons; a silane of up to 25 carbons; a nitrogen heterocycle of up to 25 carbons; and wherein $R^8$ is a group selected from the above or is carbonyl.

8. The compound of claim 1, wherein $L^1$ is nitrogen, phosphorus, arsenic, antimony, or bismuth.

9. The compound of claim 8, wherein $L^1$ is phosphorus.

10. The compound of claim 1, wherein M is copper, zinc, or tin.

11. The compound of claim 10, wherein M is copper.

12. The compound of claim 11, wherein M is copper (I).

13. The compound of claim 1, wherein M is copper (I), n is 2, and $R^4$ is Cl.

14. A compound of claim 1, wherein M is Cu(I), $R^4$ is Cl, x is 2, n is 3, m is 1, $L^1$ is P, $R^2$ and $R^3$ are ethoxy groups, and $R^1$ is a methacrylate group.

15. A controlled release composition comprising a compound of claim 1.

16. The composition of claim 15, further comprising an active agent.

17. The compound of claim 1, where $L^1$ is an element of Group 13 of the Periodic Table.

18. The compound of claim 1, wherein $L^1$ is an element of Group 14 of the Periodic Table.

19. The compound of claim 1, wherein $L^1$ is an element of Group 16 of the Periodic Table.

20. The compound of claim 1, wherein M is a metal element of Group 13 of the Periodic Table.

21. The compound of claim 1, wherein M is a metal element of Group 14 of the Periodic Table.

22. The compound of claim 1, wherein M is a metal element of Group 15 of the Periodic Table.

23. The compound of claim 1, wherein M is a metal element of Group 16 of the Periodic Table.

24. The compound of claim 1, wherein M is a transition element of the Periodic Table.

25. The compound of claim 1, wherein $R^1$ is an acrylate or methacrylate group.

26. The compound of claim 1, wherein $R^2$ and $R^3$, which can be the same or different, are an alkyl or alkoxy group of up to 15 carbons or an aryl or aryloxy group of up to 25 carbons.

27. The compound of claim 1, wherein $R^4$ is a halogen, a cyanate, an isocyanate, or a thiocyanate.

28. The compound of claim 1, wherein $L^2$ is a trivalent phosphorus, trivalent arsenic, or a trivalent antimony compound or a divalent sulfur, divalent selenium or a divalent tellurium compound when bonded to three substituents for trivalent compounds or two substituents for divalent compounds excluding the bond to M.

29. The compound of claim 1, wherein $L^2$ is a substituted or unsubstituted aryl or alkyl isocyanide; a carbonyl or carbon monoxide; a thiocarbonyl or carbon monosulfide; a nitrosyl; a substituted or unsubstituted amine; a nitrile with a substituted or unsubstituted alkyl or aryl; a coordinating solvent; a substituted or unsubstituted unsaturated alkyl or aryl which bonds to the M mainly through a pi-bond.

30. The compound of claim 1, represented by formula (II):

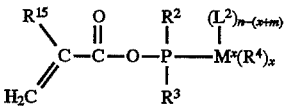

wherein $R^{15}$ represents a hydrogen or a linear alkyl group of up to 6 carbons, and $R^2$, $R^3$, $L^2$, M, $R^4$, x, n, and m have the same meanings as in formula (I).

31. The compound of claim 1, represented by the formula:

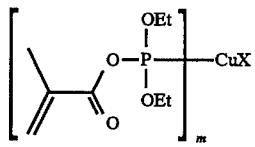

wherein X is Cl, SCN, or thiophenyl and m=1 when X is Cl, m=2 when X is SCN, and m=3 when X is thiophenyl.

32. The compound of claim 1, wherein $R^2$ and $R^3$ interconnect to form a chelating ligand.

33. The compound of claim 32, wherein said chelating ligand has the structure

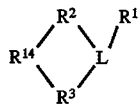

wherein $R^2$ and $R^3$ are alkyl or alkoxy groups of up to 15 carbon atoms; or aryl or aryloxy groups of up to 25 carbons; $R^{14}$ is an alkyl group of up to 6 carbons or represents a bond between $R^2$ and $R^3$, and $R^1$ is as defined in claim 1.

34. The compound of claim 1, wherein $R^4$ is an alkyl group, a thioalkyl having up to 15 carbons, a thioaryl having up to 25 carbons, a sulfur containing heterocycle with up to 25 carbons, an aryloxide with up to 25 carbons, an alkoxide with up to 15 carbons, an oxygen containing heterocycle with up to 25 carbons, a cyclopentadienyl with up to 30 carbons, or an acetylacetonate with optional substitution of at least one of any of the hydrogens on any of the carbons therein with a halogen.

35. The compound of claim 1, wherein said alkyl of up to 15 carbons is a substituted alkyl group wherein at least one hydrogen is replaced with at least one halogen; at least one oxygen, nitrogen, or sulfur, wherein the oxygen optionally has at least one additional carbon, nitrogen, or sulfur attached to the oxygen, the nitrogen optionally has at least one additional carbon, nitrogen, or sulfur attached to the nitrogen, or the sulfur optionally has at least one additional carbon, nitrogen, or sulfur attached to the sulfur.

36. The compound of claim 35, wherein said substituted alkyl group is an amine, an alcohol, an acid, an ester, a ketone, a sulfide, a sulfone, a sulfoxide, an isocyanate, a cyanate, a thiocyanate, a nitrile, or a nitrosone.

37. The compound of claim 1, wherein said aryl of up to 30 carbons is a substituted aryl group wherein at least one nitrogen-containing ligand, at least one oxygen-containing ligand, at least one sulfur-containing ligand, or an alkyl group is added to at least one aryl ring carbon.

38. The compound of claim 3, wherein said alkyl of up to 25 carbons is a substituted alkyl group wherein at least one hydrogen is replaced with at least one halogen, at least one oxygen, nitrogen, or sulfur, wherein the oxygen optionally has at least one additional carbon, nitrogen, or sulfur attached to the oxygen, the nitrogen optionally has at least one additional carbon, nitrogen, or sulfur attached to the nitrogen, or the sulfur optionally has at least one additional carbon, nitrogen, or sulfur attached to the sulfur.

39. The compound of claim 38, wherein said substituted alkyl group is an amine, an alcohol, an acid, an ester, a ketone, a sulfide, a sulfone, a sulfoxide, an isocyanate, a cyanate, a thiocyanate, a nitrile, or a nitrosone.

40. The compound of claim 3, wherein said aryl of up to 25 carbons is a substituted aryl group wherein at least one nitrogen-containing ligand, at least one oxygen-containing ligand, at least one sulfur-containing ligand, or an alkyl group is added to at least one aryl ring carbon.

41. The compound of claim 7, wherein said alkyl of up to 25 carbons is a substituted alkyl group wherein at least one hydrogen is replaced with at least one halogen, at least one oxygen, nitrogen, or sulfur, wherein the oxygen optionally has at least one additional carbon, nitrogen, or sulfur attached to the oxygen, the nitrogen optionally has at least one additional carbon, nitrogen, or sulfur attached to the nitrogen, or the sulfur optionally has at least one additional carbon, nitrogen, or sulfur attached to the sulfur.

42. The compound of claim 41, wherein said substituted alkyl group is an amine, an alcohol, an acid, an ester, a ketone, a sulfide, a sulfone, a sulfoxide, an isocyanate, a cyanate, a thiocyanate, a nitrile, or a nitrosone.

43. The compound of claim 7, wherein said aryl of up to 25 carbons is a substituted aryl group wherein at least one nitrogen-containing ligand, at least one oxygen-containing ligand, at least one sulfur-containing ligand, or an alkyl group is added to at least one aryl ring carbon.

* * * * *